(12) United States Patent
Robinson et al.

(10) Patent No.: US 11,551,799 B1
(45) Date of Patent: Jan. 10, 2023

(54) MULTI-STAGE RELEASE CANNABINOID COMPOSITIONS

(71) Applicant: Green Sky Creations LLC, Seattle, WA (US)

(72) Inventors: Simon Robinson, Seattle, WA (US); Brad Douglass, Seattle, WA (US)

(73) Assignee: Green Sky Creations LLC, Seattle, WA (US)

( * ) Notice: Subject to any disclaimer, the term of this patent is extended or adjusted under 35 U.S.C. 154(b) by 0 days.

(21) Appl. No.: 17/713,994

(22) Filed: Apr. 5, 2022

(51) Int. Cl.
| | |
|---|---|
| *G16H 20/10* | (2018.01) |
| *A61K 9/48* | (2006.01) |
| *G16H 50/50* | (2018.01) |
| *A61K 31/352* | (2006.01) |
| *A61B 5/00* | (2006.01) |
| *A61K 31/05* | (2006.01) |

(52) U.S. Cl.
CPC ........... *G16H 20/10* (2018.01); *A61B 5/4848* (2013.01); *A61K 9/48* (2013.01); *A61K 31/05* (2013.01); *A61K 31/352* (2013.01); *G16H 50/50* (2018.01)

(58) Field of Classification Search
CPC ...... G16H 20/10; G16H 50/50; A61B 5/4848; A61K 9/48; A61K 31/05; A61K 31/352
See application file for complete search history.

(56) References Cited

U.S. PATENT DOCUMENTS

2020/0372993 A1* 11/2020 Chu ................... G16H 40/63

FOREIGN PATENT DOCUMENTS

WO    WO-2020227440 A1 * 11/2020 ........... A61K 36/185

OTHER PUBLICATIONS

Wiskerke, Joost; Stoop, Nicky; Schetters, Dustin; Schoffelmeer, Anton N M; Pattij, Tommy. "Cannabinoid CB1 Receptor Activation Mediates the Opposing Effects of Amphetamine on Impulsive Action and Impulsive Choice." PLoS One6.10: e25856. Public Library of Science. (Oct. 7, 2011) (Year: 2011).*

* cited by examiner

*Primary Examiner* — Linh Giang Le
(74) *Attorney, Agent, or Firm* — Perkins Coie LLP

(57) ABSTRACT

The present disclosure provides a pharmaceutical composition for multi-stage release of psychoactive substances including cannabinoids. The pharmaceutical composition comprises two or more staged compositions having different release profiles or different release time such that the one or more active agents in each of the two or more staged compositions are released into the subject's blood stream at different time points.

23 Claims, 11 Drawing Sheets

FIG 2

| Composition Database | |
|---|---|
| First Stage | Second Stage |
| 10 mg of THC and 10 mg of CBD | 20 mg of CBD and 5 mg of THC |
| 5 mg of THC and 50 mg of CBD | 30 mg of CBD and 0 mg of THC |
| 5 mg of THC and 5 mg of THCA | 50 mg CBD |
| 15 mg of CBN | 2 mg THC and 2 mg CBD |
| 25 mg delta-8 of THC | 25 mg of delta-8 THC |
| 100 mg CBG and 10 mg delta-9 THC | 50 mg CBG |
| 0 mg of THC or CBD | 20 mg delta-9 THC |
| 50 mg CBC | 50 mg THC |
| 2.5 mg delta-8 THC | 2.5 mg CBD |
| 10 mg of THCV and 10 mg CBDV | 20 mg of CBDV and 5 mg of THCV |
| 50 mg of CBGA and 10 mg CBNA | 10 mg CBNA and 10 mg CBGA |
| 5 mg of THC and 10 mg HHC | 5 mg CBD and 10 mg HHC |
| 10 mg of THC and 10 mg of CBE | 0 mg of THC and 5 mg of CBD |

FIG 3

| Analgesic Database | |
|---|---|
| S. No. | Analgesic |
| 1 | Acetaminophen |
| 2 | Naproxen |
| 3 | Ibuprofen |
| 4 | Aspirin |
| 5 | Bromfenac |
| 6 | Etodolac |
| 7 | Oxaprozin |
| 8 | Loxoprofen |
| 9 | Piroxicam |
| 10 | Droxicam |
| 11 | Sulindac |
| 12 | Nalfon |

FIG 4

| Bioavailability Enhancer Database | |
|---|---|
| S. No. | Bioavailability Enhancer |
| 1 | N-acylated fatty amino acid |
| 2 | Green tea catechins |
| 3 | Piperine |
| 4 | DMSO |
| 5 | Soy lecithin |

FIG 5

| Pharmaceutical Composition Database ||
|---|---|
| S. No. | Pharmaceutical Composition |
| 1 | Methyl acrylate-methacrylic acid copolymers |
| 2 | Cellulose acetate phthalate (CAP) |
| 3 | Cellulose acetate succinate |
| 4 | Hydroxypropyl methyl cellulose phthalate |
| 5 | Hydroxypropyl methyl cellulose acetate succinate (hypromellose acetate succinate) |
| 6 | Polyvinyl acetate phthalate (PVAP) |
| 7 | Methyl methacrylate-methacrylic acid copolymers |
| 8 | Shellac |
| 9 | Cellulose acetate trimellitate |
| 10 | Sodium alginate |
| 11 | Zein |
| 12 | Enteric coating aqueous solution (ethylcellulose, medium chain triglycerides [coconut], oleic acid, sodium alginate, stearic acid) (coated softgels) |

FIG 6

| Sleep Composition database | | |
|---|---|---|
| S. No. | Sleep Composition | |
| | Pharmaceutical Composition | Botanical Extract |
| 1 | Doxepin (Silenor) | Valerian |
| 2 | Estazolam | Rosemary |
| 3 | Eszopiclone (Lunesta) | St. John's Wort |
| 4 | Ramelteon (Rozerem) | Hawthorn |
| 5 | Temazepam (Restoril) | Chamomile |
| 6 | Triazolam (Halcion) | Hop |
| 7 | Zaleplon (Sonata) | Lavender |
| 8 | Zolpidem (Ambien, Edluar, Intermezzo, Zolpimist) | Valerian and Hops |
| 9 | Zolpidem extended release (Ambien CR) | Magnolia Bark |
| 10 | Suvorexant (Belsomra) | Passionflower |

FIG 9
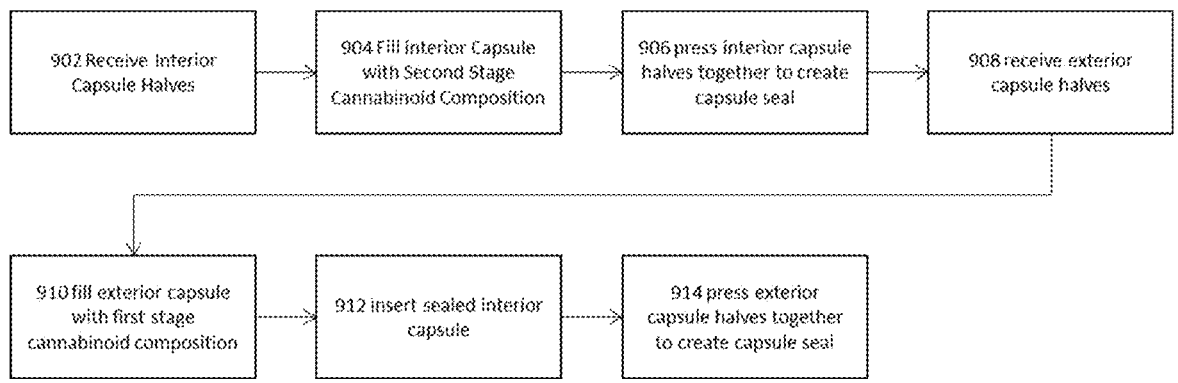
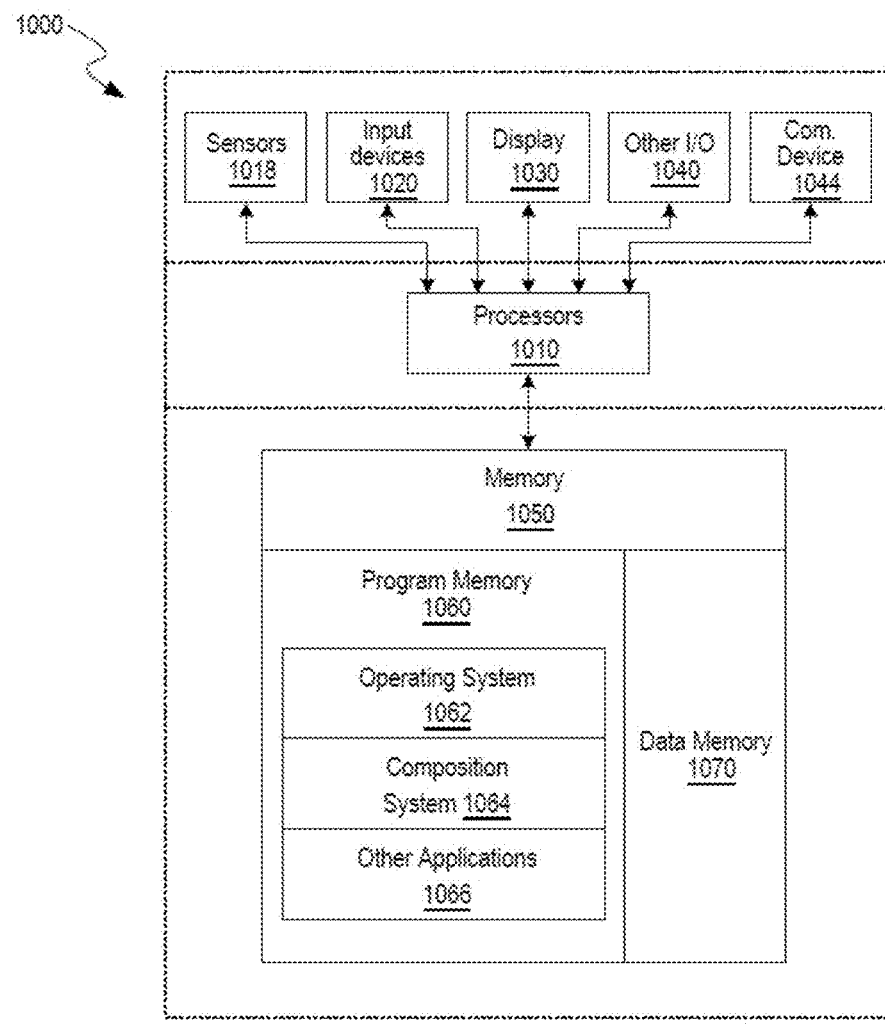
*FIG. 10*

MULTI-STAGE RELEASE CANNABINOID COMPOSITIONS

TECHNICAL FIELD

The present disclosure is related to cannabinoid compositions having enhanced bioavailability. The cannabinoid compositions disclosed herein can further comprise other psychoactive ingredients and possess improved multi-stage bioavailability, physiological targeting, and delayed onset.

BACKGROUND

Food products containing edible cannabis extract have emerged as a popular and lucrative facet of the legalized market for both recreational and medicinal cannabis. The many formulations of cannabis extracts used in edibles present a unique regulatory challenge for policy makers. Although edibles are often considered a safe, discreet, and effective means of attaining the therapeutic and/or intoxicating effects of cannabis without exposure to the potentially harmful risks of cannabis smoking, there has been limited research evaluating how ingestion differs from other methods of cannabis administration in terms of therapeutic efficacy, subjective effects, and safety. The most prominent difference between ingestion and inhalation as routes of administration for cannabis extracts and many other psychoactive plant preparations (e.g., psilocybin-containing fungi) is the delayed onset of drug-effect with ingestion. Uninitiated consumers often do not understand or expect this and may consume a greater than intended amount of the active drug before the drug has taken effect, which can result in profoundly physical or psychological adverse effects.

Accordingly, there is a need to develop cannabinoid compositions having improved, better controlled bioavailability. The compositions disclosed herein satisfy the need in the art.

SUMMARY

This disclosure relates to a formulation formulated into a single dosage form, comprising two or more compositions staged for release at different times or having different release profiles. One or more staged composition comprises one or more active agents such as cannabinoids including THC and CBD, analgesics, sleeping aids, and botanical extracts. In some embodiments, one or more staged composition may comprise one or more bioavailability enhancers. In some embodiments, the formulation is formulated into a pill, a tablet, a capsule, a topical patch, a transdermal patch, a transmucosal patch, a lozenge, or a suppository. In some embodiments, the formulation further comprises one or more coatings between the two or more staged compositions.

In a related aspect, this disclosure relates to a method of delivering compositions staged for release at different time or having different release profiles by a single administration of the formulation disclosed herein.

BRIEF DESCRIPTION OF THE DRAWINGS

FIG. 2 illustrates a composition database, according to an embodiment.

FIG. 3 illustrates an analgesic database, according to an embodiment.

FIG. 4 illustrates a bioavailability database, according to an embodiment.

FIG. 5 illustrates a pharmaceutical database, according to an embodiment.

FIG. 6 illustrates a sleep database, according to an embodiment.

FIG. 9 illustrates a flowchart showing a method for manufacturing capsule filling module, according to an embodiment.

FIG. 10 is a block diagram illustrating an overview of a system on which some implementations of the disclosed technology can operate, according to an embodiment.

DETAILED DESCRIPTION

Figure 1:
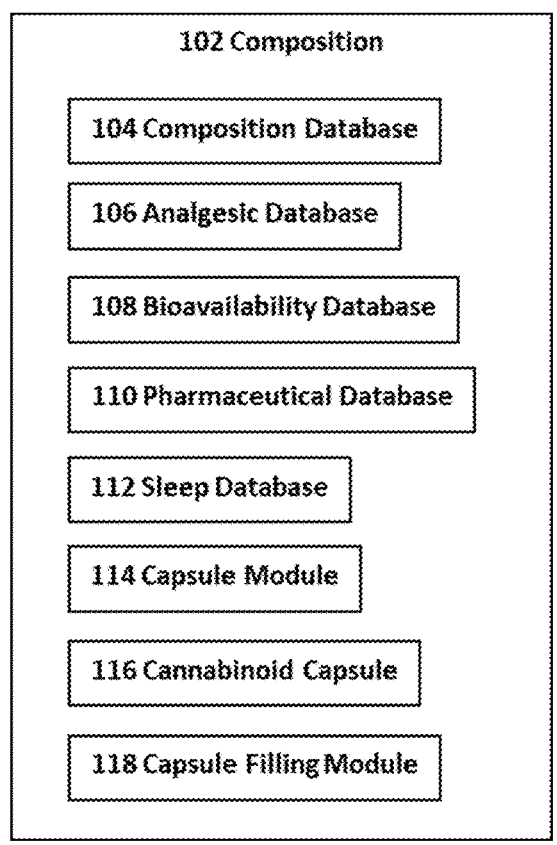
FIG. 1 illustrates a system for selecting compositions for multi-stage release of cannabinoids, according to an embodiment.

The pharmacokinetic profile of a drug substance includes absorption, which varies depending on route of administration, distribution throughout the body, metabolism by the liver and extra-hepatic tissues such as the gut microbiome, and elimination in the feces, urine, sweat, oral fluid, and hair. Often the acronym ADME is used to abbreviate these four main considerations of pharmacokinetics and pharmacology—absorption, distribution, metabolism, and elimination. Pharmacokinetic processes are dynamic, may change over time, and can be affected by the frequency and magnitude of drug exposure as well as other environmental considerations, such as what has been eaten or the physical condition of the epidermis, depending on the route of administration.

At present, it is not currently possible to administer two differing cannabinoid compositions at the same time while pre-programming selective delays in their impact on plasma levels and respective effects. For example, it may be advantageous to administer a cannabinoid treatment wherein a single dose provides a ratio of THC:CBD in a 10:1 proportion during the first hour of onset, and a ratio of THC:CBD of 1:1 during the second hour of onset. However, due to the challenges associated with the pharmacokinetics of ingested cannabinoids, simply delaying the second dose by an hour may not have the intended effect or may not maintain blood concentrations within a preferred range. Similarly, timing of dosing may present challenges for certain patients and caregivers. There exists a need for a method of introducing cannabinoid and other psychoactive compounds in which the onset and sunset of effects can be both programmed and managed using various bioavailability enhancements and triggers when administering a plurality of psychoactive compounds at once.

Disclosed herein is a means for administering a plurality of psychoactive compounds, including cannabinoid compositions, in a single dose that can have disparate, but controlled initiations of onset. In certain embodiments, a single treatment is administered to a subject to elicit various therapeutic effects, for example, alleviating pain, providing energizing effects, increasing appetite, assisting with sleep, stimulating introspection, aiding meditative practice, or some combination of the therapeutic effects of cannabinoids and other psychoactive substance, at various times and in various parts of the subject's digestive tract. In certain embodiments, the subject is a mammal. In certain embodiments, the subject is human.

In one aspect, disclosed herein is a formulation comprising two or more compositions staged for release at a different time or with different release profiles. For example, the formulation comprises a first staged composition comprising one or more active agents, and a second staged composition comprising one or more active agents, wherein the first staged composition and the second staged composition have different release profiles or staged for release at different time. For example, the active agent can be formulated for immediate release, controlled release, sustained release, or delayed release. In another example, the active agent can be embedded into different layers such that the active agent in the outer layer is released first, and then the active agent embedded in an inner layer or inside the core can only be released after the outer layer is completely or partially dissolved, degraded, or disintegrated to expose the inner layer or the core. In yet another example, the first staged composition comprises microcapsules or beadlets and the second staged composition comprises one or more large capsules or softgels that completely encapsulates the first staged composition.

The one or more active agents in the first staged composition may be the same or different from the one or more active agents in the second staged composition. For example, the first staged composition is used for alleviating pain quickly and second staged composition is used for managing or maintaining the pain state created by the first stage composition after the first stage composition is fully metabolized. The formulation provides a solution to pain management and controlling the release of a plurality of cannabinoid or other physiologically active or functional compounds in vivo. Further, the formulation helps in administering two or more distinct compositions at the same time where a later stage composition has a pre-defined time delay in entering the patient's bloodstream relative to the earlier stage composition. Various active agents can be included in the formulation for a desirable stage of release. These active agents include but are not limited to cannabinoids such as THC and CBD, analgesics such as acetaminophen, naproxen, ibuprofen, aspirin, bromfenac, etodolac, oxaprozin, loxoprofen, piroxicam, droxicam, sulindac, and nalfon, sleeping aids such as doxepin (Silenor), estazolam, eszolam, eszopiclone (Lunesta), ramelteon (Rozerem), temazepam (Restoril), triazolam (Halcion), zaleplon (Sonata), zolpidem (Ambien, Edluar, Intermezzo, Zolpimist) and zolpidem extended release (Ambien CR), and suvorexant (Belsomra), and botanical extracts such as valerian, rosemary, St. John's wort, hawthorn, chamomile, hop, lavender, valerian and hops, magnolia bark, and passion flower. In some embodiments, one or more staged composition comprises a bioavailability enhancer such as N-acylated fatty amino acid, green tea catechins, piperine, DMSO, and soy lecithin.

In some embodiments, the formulation is formulated in an oral dosage form including a solid oral dosage form, a liquid oral dosage form, or a combination thereof. Various oral dosage forms may be used such as a pill, a tablet, and a capsule. In some embodiments, the formulation comprising a core and at least one layer encapsulating the core, wherein the core comprises a first staged composition and the layer comprises a second staged composition. In some embodiments, the formulation comprising a core and one or more layers encapsulating the core, wherein each layer and the core comprise compositions having different release profiles or different release time thereby to obtain a multi-stage formulation. In some embodiments, the formulation comprises a coating over the core to separate the core from the encapsulating layer(s). In some embodiments, the formulation comprises one or more coatings to separate the layers. The coating can further modify the release profile of the core and each layer. In some embodiments, the thickness of the core and each layer may vary or be independently adjusted to contain various amounts of active agents and/or to achieve desirable release profiles. In some embodiments, the solid dosage form and the liquid dosage form may be combined, for example, the core is in a liquid dosage form or semi-liquid dosage form including but not limited to liquid, gel, emulsion, and the encapsulating layer is in a solid dosage form. In some embodiments, the solid dosage form may take the form of beadlets or microcapsules ensconced within a second liquid dosage form which is then encapsulated by an outer capsule material, softgel, or other coating. In some embodiments, more than one beadlet composition or type may be utilized. In some embodiments, the formulation is formulated into a topical patch comprising multiple layers, a transdermal patch comprising multiple layers or a transmucosal patch comprising multiple layers, wherein each layer is released at different time or comprises compositions of different release profiles. In some embodiments, the patch includes microcapsules or active dots embedded within one or more layers of the topical, transdermal or transmucosal patch. Other dosage forms include lozenges, suppositories, etc.

In some embodiments, the first staged composition has a first thickness or time delay and the second staged composition has a second thickness or time delay. In some embodiments, a multi-stage formulation disclosed herein comprises a first staged oral cannabinoid composition which may be present in an oil-in-water emulsion containing one or more substances that serve to enhance absorption into biological tissue (such as surfactants, amino acids, cyclodextrins, active transporters, phages), and a second staged oral composition capable of activating the bioavailability enhancement of the first staged composition. In some embodiments, the time delay between administration of the first staged composition and administration of the second staged composition may modify the bioavailability of the cannabinoid administered in the first staged composition. In some embodiments, the multi-stage formulation increases the bioavailability of a cannabinoid or another analgesic pharmaceutical by altering the physical properties of the cannabinoid through aggregation phenomena or chemically through the creation of a molecular variant of the cannabinoid. Myristoylation, palmitorylation and palmitoleoylation are examples of acylation reactions which can for example, convert nitrogen- or oxygen-containing groups into their related acylated variants (e.g., amino acids converting into N-acylated amino acids). Another example includes methylation using methylating agents such as S-adenosylmethionine (SAM-e), trimethylglycine, and tetrahydrofolate which can for example create methyl ether or methyl ester variants of the original bioactive compound. In some embodiments, the multi-stage formulation is a multi-layered pill, tablet, or capsule including a cannabinoid and a formulation that comprises bioavailability enhancers.

In some embodiments, the formulation comprises a first layer comprising a first composition, and at least a second layer comprising a second composition, wherein the second composition may contain one or more active agents, for example, active cannabinoids and the first composition may contain one or more active agents such as NSAIDs. In some embodiments, the multi-stage composition comprises a first layer comprising a first composition comprising a psychoactive compound such as dimethyltryptamine (DMT) as an active agent, and at least a second layer comprising a second composition comprising active compounds that alter the effect or metabolic response to the first composition, such as monoamine oxidase inhibitors (e.g., harmine, harmaline, quercetin, berberine).

In some embodiments, the formulation may facilitate a multilayered capsule for sleep including a cannabinoid and a bioavailability enhancing formulation. Wherein the method involves administering a capsule with at least two layers, the at least two layers comprising at least two compositions, the first composition comprising a cannabinoid (e.g., CBD) and the second composition comprising a botanical or pharmaceutical substance indicated in aiding sleep or acting on or with the first composition to accentuate, activate, or synergize with the contents of the first composition. In another embodiment, the formulated capsule may be a multi-layered capsule for sleep stages including a cannabinoid and a bioavailability enhancer. Wherein the method involves administering a capsule with at least two layers, the at least two layers comprising at least two compositions, the first composition comprised of psychoactive compounds and other botanical or therapeutic substances selected for a first sleep stage, the second composition comprised of psychoactive compounds and other botanical or therapeutic substances selected for a second sleep stage. Further, the composition 102 may determine the bioavailability enhancer or bioavailability delayer to enhance, extend or program in time the activity of the first and second stage psychoactive compound composition.

In some embodiments, the formulation may be a multi-layered pill, tablet, or capsule for aiding sleep including a cannabinoid and a bioavailability enhancing formulation. For example, the formulation comprises at least two layers, the at least two layers comprising at least two compositions, the first composition comprising a cannabinoid (e.g., CBD) and the second composition comprising a botanical or pharmaceutical substance indicated in aiding sleep or acting on or with the first composition to accentuate, activate, or synergize with the contents of the first composition. In some embodiments, the formulation comprising a cannabinoid and a bioavailability enhancer is formulated for different sleep stages. For example, the formulation comprises at least two layers, the at least two layers comprising at least two compositions, the first composition comprised of psychoactive compounds and other botanical or pharmaceutical substances selected for a first sleep stage, the second composition comprised of psychoactive compounds and other botanical or pharmaceutical substances selected for a second sleep stage. Further, the formulation further comprises one or more bioavailability enhancers to enhance the activity of the first and second stage psychoactive compound composition.

In some embodiments, a first staged composition comprises a modulator that modulates the metabolic machinery of the organism to impact the pharmacokinetics of the active agent contained in a second staged composition. The modulator may be released into the blood stream of the subject before or after release of the active agent. For example, the first staged composition may comprise a phase 1 and/or phase 2 inhibitor that is first introduced in the body prior to the introduction of a cannabinoid (e.g., delta-9 THC) into the body as a means of inhibiting the metabolism of the cannabinoid to an inactive metabolite thus maintaining a pharmacologically relevant blood concentration range of the cannabinoid in plasma for a longer duration. Phase I detoxification yields, in general, more polar and more water-soluble metabolites, but that may retain pharmacological activity by often adding an oxygen-functional group to a lipophilic substance. Many of the end products of phase I detoxification also become substrates for phase II detoxification. Examples of phase I transformations include oxidation, reduction and hydrolysis reactions. Phase II detoxification yields a large polar metabolite by adding endogenous hydrophilic groups to form water-soluble inactive compounds that can be excreted by the body. Examples of phase II transformations include methylation, glucuronidation, acetylation, sulfation, etc. Delta-9 THC is lipophilic and quickly undergoes phase 1 detoxification to 11-hydroxy-delta-9 THC in the liver. 11-hydroxy-delta-9 THC is still active at CB1 receptors and can undergo further phase 1 detoxification—a second oxidative step—into 11-nor-carboxy-delta-9-THC, which is not active at CB1 receptors. Both 11-hydroxy and 11-nor-carboxy THC metabolites are then glucuronidated (phase II) before they are excreted from the body in urine. (See www.ncbi.nlm.gov/books/NBK544353/.) Specific phase 1 inhibitors and inducers can be used to tailor what drug metabolizing reactions take place such that one can either accelerate or decelerate the half-life of an active substance or metabolite. Various subclasses of the super-family of cytochrome P450 (CYP) enzymes can be targeted including CYP1A2, CYP2B6, CYP2C8, CYP2C9, CYP2C19, CYP2D6, CYP3A4/5, and others. Inhibitors of CYP enzymes include piperine, narigenin, caffeine, niacin, bergamottin, and *Hypericum perforatum* (St. John's Wort), *Allium sativum* (garlic), *Curcuma longa* (turmeric). Inducers of CYP enzymes include berberine, St. John's Wort, ethanol, and others including various drug substances (Hakkola et al., "Inhibition and induction of CYP enzymes in humans: an update," Archives of Toxicology 94: 3671-3722 (2020)). In another example, a first staged composition comprises a monoamine oxidase inhibitor, and a second staged composition comprises a tryptamine, such as psilocin, psilocybin, dimethyltryptamine, or 5-MeO-dimethyltryptamine. In another example, a first stage composition comprises a monoamine oxidase inducer and a second stage composition comprises a phenethylamine, such as amphetamine, methylenedioxymethamphetamine, or 4-bromo-2,5-dimethoxyphenethylamine.

In some embodiments, the formulation disclosed herein may facilitate a multi-layered topical, transdermal or transmucosal delivery of a cannabinoid and/or psychoactive substance with targeted bioavailability enhancement or an altered metabolic response. In some embodiments, this disclosure relates to a topical patch, a transdermal patch or mucosal pouch, which comprises at least two layers, each layer comprising one of at least two compositions, wherein a first composition contains a cannabinoid and/or psychoactive, and a second composition contains a bioavailability enhancer.

FIG. 1 illustrates a composition system 102 for multi-stage release of cannabinoids, according to an embodiment. The composition system 102 may also utilize a composition database 104 containing composition data, including the first staged and second staged compositions and their quantity (e.g., quantity measured in mg). In one embodiment, the composition system 102 may be coupled to an analgesic database 106 to add analgesic or non-steroidal anti-inflammatory substances in the other cannabinoid or psychoactive compound composition. In another embodiment, the composition system 102 may be coupled to a sleep composition database 112 to pair a sleep composition with the cannabinoid or other psychoactive compound composition. In one case, a plurality of compositions 102 might be available and the practitioner may recommend a particular composition from the composition system 102 to the subject. In another case, the composition may be customized for each subject by the practitioner based on the sleep stages of the subject. For example, the two-stage cannabinoid composition is formulated from the first staged composition (i.e., e.g., 10 mg of THC and 10 mg of CBD, 100 mg of ibuprofen) and a bioavailability enhancer (e.g., N-acylated fatty amino acid) and second staged composition (e.g., 5 mg of THC and 50 mg of CBD, 100 mg of acetaminophen) and a second bioavailability enhancer (e.g., piperine). Further, embodiments may utilize the composition database 104, which may include different cannabinoid compositions for the first and second staged compositions. Further, embodiments may utilize the analgesic or non-steroidal anti-inflammatory drugs (NSAID) database 106, which may be coupled to the capsule formulation engine module 114. Further, analgesic compounds may be used with the first staged composition, second staged composition, or in both stages. For example, the analgesic compounds may be acetaminophen, naproxen, ibuprofen, aspirin, Bromfenac, Etodolac, Oxaprozin, Loxoprofen, Piroxicam, Droxicam, Sulindac, Nalfon.

Further, embodiments may include a bioavailability enhancer database 108, which may be coupled to the capsule formulation module 114. Further, embodiments may include a formulation database 110, which may be coupled to the capsule formulation module 114. Further, embodiments may include the sleep composition database 112, which may be coupled to the capsule formulation module 114 to add a sleep composition in the cannabinoid composition. Further, embodiments may include the capsule formulation module 114 which formulates a cannabinoid capsule for the subject. Further, embodiments may include a cannabinoid capsule 116 which is an example of an article of manufacture which may include the composition 102. The cannabinoid capsule 116 including an interior capsule which is enclosed within an exterior capsule such that when the cannabinoid capsule 116 is ingested, it will first dissolve the exterior capsule, releasing a first staged cannabinoid composition and the interior capsule, and after a period of time the interior capsule will dissolve releasing a second staged cannabinoid composition. Further, embodiments may include a capsule filling module 118 which is the process by which a cannabinoid capsule 116 is assembled wherein an interior capsule is filled with a second staged cannabinoid composition and is sealed before being inserted into an exterior capsule filled with a first staged cannabinoid composition after which the exterior capsule is sealed. Example composition systems, components, and databases (e.g., engines) are discussed in connection with FIGS. 10-11.

FIG. 2 illustrates the composition database 104, which may include different cannabinoid or and/or psychoactive compositions for the first and second staged compositions. In one embodiment, the first and second staged cannabinoid and/or psychoactive composition may be released inside the human body according to the level of pH of the digestive tract of the human body. In an exemplary embodiment, the first staged compositions may be absorbed in the stomach having pH level 6.5 to 7.5 and the second staged compositions may be absorbed in the large or small intestine having pH level 4-10. In another embodiment, the release of the first and second staged cannabinoid composition may be a timed event. Further, the cannabinoid or and/or psychoactive composition may be released in capsule form wherein the first staged composition may be an outer coating or shell of composition. The second staged composition may be an internal composition to the capsule. In another embodiment, the cannabinoid or and/or psychoactive composition may be released in the transdermal patch form. In yet another embodiment, the cannabinoid or and/or psychoactive composition may be released in oral lozenge form. In yet another embodiment, the cannabinoid or and/or psychoactive composition may be released in suppository form. In yet another embodiment, a new form factor having a bead inside the capsule may be used for the release of two-stage cannabinoid composition. In one embodiment, the first composition may be the outer layer of the capsule, the inner liquid contents of the capsule, and the second composition may be a bead or beads floating inside the liquid contents of the capsule. In another embodiment, one of at least two compositions may be released based on the sleep stage detected from a wearable device. Further, the composition database 104 may be coupled to a capsule formulation module 114.

FIG. 3 illustrates the analgesic database 106, which may be coupled to the capsule formulation module 114. Further, an analgesic may be used with the first staged composition, second staged composition, or in both stages. For example, the analgesic may be acetaminophen, naproxen, ibuprofen, aspirin, Bromfenac, Etodolac, Oxaprozin, Loxoprofen, Piroxicam, Droxicam, Sulindac, Nalfon.

FIG. 4 illustrates the bioavailability enhancer database 108, which may be coupled to the capsule formulation module 114. In one embodiment, the bioavailability enhancer may be selected based on the desired bioavailability of the cannabinoid. In another embodiment, the bioavailability enhancer may be selected based on the delivery method for the cannabinoid composition. The delivery method may include sublingual, oral, inhalable, suppository and topical. In yet another embodiment, the bioavailability enhancer may be selected based on other factors. The other factors may include taste, the potential for allergies, side-effects, and price. Further, the bioavailability enhancer database 108 may store information related to bioavailability enhancers used in two-stage compositions. For example, the bioavailability enhancer may be N-acylated fatty amino acid, green tea catechins, piperine, DMSO, soy lecithin, amongst others.

FIG. 5 shows a formulation database 110, which may be coupled to the capsule formulation module 114. Further, the formulation may only be used with the first staged composition for delaying the release of the first staged composition. Further, the formulation database 110 may store information related to the ingredients and compositions used in the first staged composition. For example, the composition may comprise substances that support functions such as extended/controlled release and enteric coatings such as, methyl acrylate-methacrylic acid copolymers, cellulose acetate phthalate (CAP), cellulose acetate succinate, hydroxypropyl methyl cellulose phthalate, hydroxypropyl methyl cellulose acetate succinate (hypromellose acetate succinate), polyvinyl acetate phthalate (PVAP), methyl methacrylate-methacrylic acid copolymers, shellac, cellulose acetate trimellitate, sodium alginate, zein, enteric coating aqueous solution (ethylcellulose, medium chain triglycerides [coconut], oleic acid, sodium alginate, stearic acid) (coated softgels).

FIG. 6 illustrates the sleep composition database 112, which may be coupled to the capsule formulation module 114 to add sleep composition in the cannabinoid composition. For example, the sleep compositions may comprise extracts or other preparations of botanicals, such as Valerian, Rosemary, St. John's Wort, Hawthorn, Chamomile, Hops, Lavender, Magnolia Bark, and Passionflower. Further, the composition may comprise Doxepin (Silenor), Estazolam, Eszopiclone (Lunesta), Ramelteon (Rozerem), Temazepam (Restoril), Triazolam (Halcion), Zaleplon (Sonata), Zolpidem (Ambien, Edluar, Intermezzo, Zolpimist), Zolpidem extended release (Ambien CR), Suvorexant (Belsomra).

Figure 7:
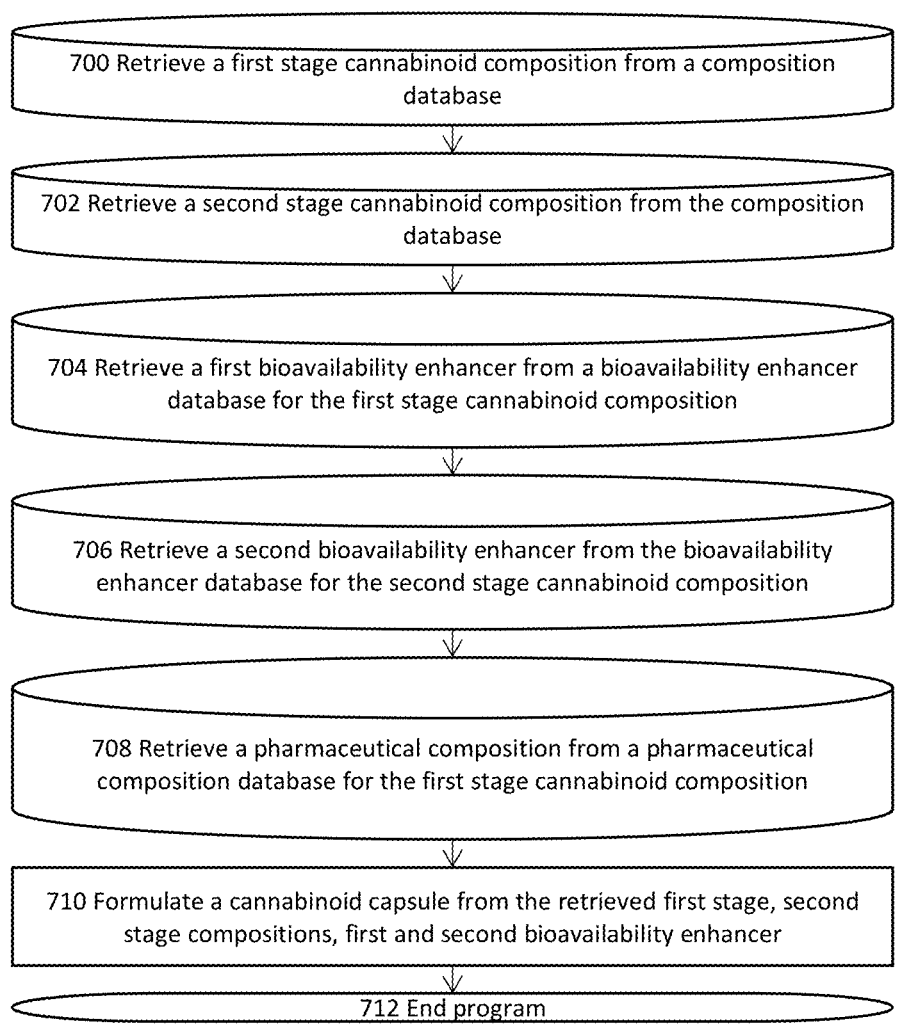
FIG. 7 illustrates a flowchart showing a method for formulating a capsule, according to an embodiment.

FIG. 7 illustrates a flowchart of a method for formulating a capsule, according to an embodiment. Embodiments may use the capsule module 114, to formulate a cannabinoid or and/or psychoactive capsule for the subject by selecting specific excipients and other nonactive ingredients that are compatible with the active ingredients. The method can be used for personalized healthcare to, for example, provide patient-specific compositions, or composition form based on, for example, the patient's health status, electronic medical records, physician input, etc. A healthcare provider can design formulations for achieving target personalized outcomes.

At first, the capsule formulation module 114 may retrieve a first staged cannabinoid or and/or psychoactive composition from the composition database 104. The cannabinoid or and/or psychoactive composition can be selected based on the patient's condition, sensitivity to active agents, etc. For example, the capsule formulation module 114 retrieves the first staged cannabinoid or and/or psychoactive composition i.e., 10 mg of THC and 10 mg of CBD or 20 mg of psilocybin from the composition database 104. In one embodiment, the capsule formulation module 114 may add an analgesic or NSAID composition from the analgesic database 106 to the first staged cannabinoid composition. For example, the capsule formulation module 114 adds 100 mg of ibuprofen from the analgesic database 106 to the first staged cannabinoid composition. Further, the capsule formulation module 114 may retrieve a second staged cannabinoid composition from the composition database 104. For example, the capsule formulation module 114 retrieves the second staged cannabinoid composition i.e., 5 mg of THC and 50 mg of CBD from the composition database 104. In one embodiment, the capsule formulation module 114 may add an analgesic or NSAID composition from the analgesic database 106 to the second staged cannabinoid or and/or psychoactive composition. For example, the capsule formulation module 114 adds 100 mg of acetaminophen from the analgesic database 106 to the second staged cannabinoid composition. Further, the capsule formulation module 114 may retrieve a first bioavailability enhancer from the bioavailability enhancer database 108 for the first staged cannabinoid composition. For example, the capsule formulation module 114 retrieves the bioavailability enhancer i.e., N-acylated fatty amino acid from the bioavailability enhancer database 108 as an effective adjuvant to the first staged cannabinoid or and/or psychoactive composition. Further, the capsule formulation module 114 may retrieve a second bioavailability enhancer from the bioavailability enhancer database 108 for a second staged cannabinoid or and/or psychoactive composition. For example, the capsule formulation module 114 retrieves the bioavailability enhancer i.e., piperine from the bioavailability enhancer database 108 for second staged cannabinoid composition. Further, the capsule formulation module 114 may retrieve the formulation from the formulation database 110 for the first staged cannabinoid composition. For example, the capsule formulation module 114 retrieves the controlled-release ingredient(s) e.g., cellulose acetate phthalate (CAP) or formulation from the formulation database 110 for delaying the absorption/dissolution of the first staged cannabinoid composition. In one embodiment, the formulation may be used for delaying the release/absorption/dissolution of the first layer (e.g., cellulose acetate phthalate (CAP)). Further, the capsule formulation module 114 may formulate a cannabinoid capsule from the retrieved first staged and second staged compositions and first and second bioavailability enhancer. For example, the capsule formulation module 114 formulates the cannabinoid capsule with the first staged composition i.e., 10 mg of THC and 10 mg of CBD, 100 mg of ibuprofen, first bioavailability enhancer N-acylated fatty amino acid and pharmaceutical composition cellulose acetate phthalate (CAP) and second staged composition i.e., 5 mg of THC and 50 mg of CBD, 100 mg of acetaminophen, second bioavailability enhancer piperine. In one embodiment, the capsule formation module 114, may formulate the cannabinoid capsule with the formulation. For example, the capsule formation module 114 formulates the cannabinoid capsule with cellulose acetate phthalate (CAP). In one example embodiment, the first composition is slowly released as the subject begins to digest the first layer. The subject may begin to feel the effects of the first composition within 30-45 minutes. As the oral capsule transits the digestive tract, the first layer eventually completely dissolves, whereupon the second layer is exposed and the contents of the second layer begin to diffuse into digestive fluids, and then the subject's body begins to absorb the second composition into the blood stream, or the second composition merely actuates its intended effect in the digestive tract without absorption into the body or blood. The subject may begin to feel the effects of the second composition approximately 1.5-2 hours after ingesting the first capsule. The oral capsule may be useful for treating acute pain quickly (via the first composition), as well as preventing the pain from returning after the first composition is fully metabolized (via the second composition). In one example embodiment, the capsule formulation module 114 may utilize the sleep composition database 112 to add sleep composition in the cannabinoid and/or psychoactive composition. Thereafter, the program ends.

Figure 8:
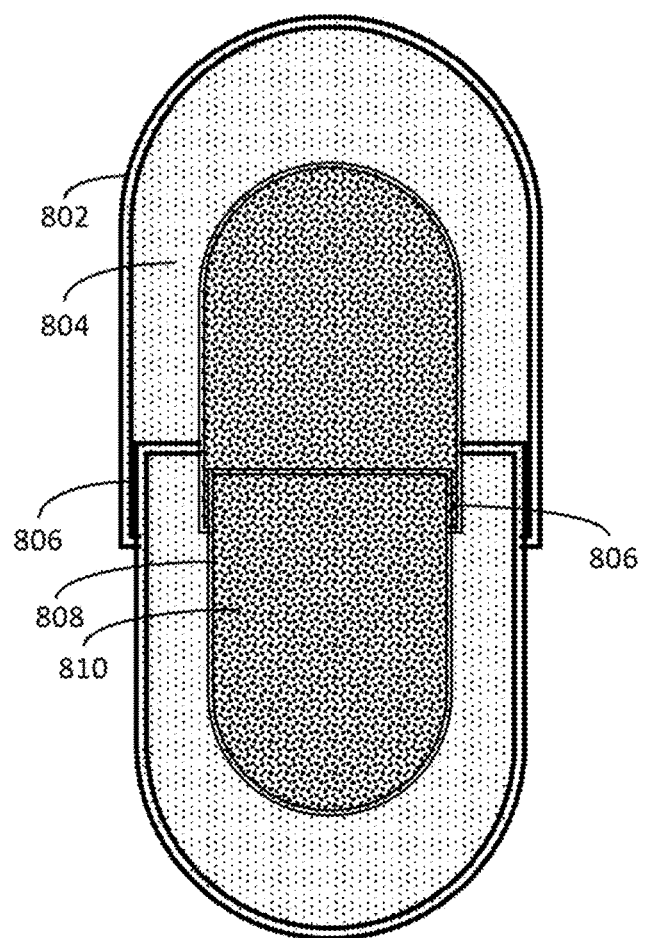
FIG. 8 illustrates a cannabinoid capsule, according to an embodiment.

FIG. 8 illustrates an example of a cannabinoid capsule 116, which is an example of a dual-stage capsule containing a first and a second cannabinoid composition. The exterior capsule wall 802 is a water-soluble shell typically comprised of gelatin or a material derived from collagen or cellulose which encapsulates a first staged cannabinoid composition 804. The exterior capsule wall 802 will dissolve in the digestive track when ingested and will release the first staged cannabinoid composition 804 contained within. The thickness of the exterior capsule wall 802 may be uniform or varied such as to control the rate at which the first staged cannabinoid composition 804 is released, and similarly when the interior capsule wall 808 is exposed to the digestive track and can be dissolved similarly. The exterior capsule wall 802 can be made thicker or incorporate additives to slow the rate at which it dissolves to delay the release of the first staged cannabinoid composition 804 or be made thinner to increase the rate at which the first staged cannabinoid composition 804 is released. The first staged cannabinoid composition 804 is a formulation of at least one cannabinoid and at least one pharmaceutical compound intended to improve the characteristics of the at least one cannabinoid, such as improving its bioavailability or complementing the desired therapeutic effects. The first staged cannabinoid composition 804 is intended for initial release to achieve a desired therapeutic effect intended to precede a second therapeutic effect to be achieved by a second staged cannabinoid composition 810. Alternatively, the first staged cannabinoid composition 804 may initiate a desired therapeutic effect which will be maintained by a second staged cannabinoid composition 810 to be released after a delay. The first staged cannabinoid composition 804 may additionally contain compounds to delay the release of either the first staged cannabinoid composition 804 or the second staged cannabinoid composition 810 by protecting the interior capsule wall 808 from being exposed to the digestive track. An example of a first staged cannabinoid composition may be a mixture of THC and CBD in a ratio of 10:1 and a ratio of cannabinoids to acetaminophen in a ratio of 1:1, such that the acetaminophen is the additive. The capsule seal 806 is where two overlapping halves of either an exterior capsule wall 802 or an interior capsule wall 808 meet and engage one another. The capsule seal 806 is typically achieved by the two halves being pressed together, creating a friction fit, by creating a mechanical indentation around the circumference of the capsule where the two halves overlap, or by adding an adhesive material to chemically bond the two capsule halves when they are pressed together. The interior capsule wall 808 is a smaller version of the exterior capsule wall 802. The interior capsule wall 808 may be comprised of similar materials as the exterior capsule wall 802 such as gelatin or a material derived from collagen or cellulose which encapsulates a second staged cannabinoid composition 804. The interior capsule wall 808 may vary in thickness or composition to achieve the desired delay and rate of release and may have different characteristics than the exterior capsule wall 802. The second staged cannabinoid composition 810 is a formulation of at least one cannabinoid and at least one pharmaceutical compound intended to improve the characteristics of the at least one cannabinoid, such as improving its bioavailability or complementing the desired therapeutic effects. The second staged cannabinoid composition 810 is typically different than the first staged cannabinoid composition 804, although they can be the same but intended to be released after a delay so as to facilitate the administration of a second dose of the first staged cannabinoid composition 804 following a delay. The second staged cannabinoid composition 810 may be comprised of the same cannabinoids and additives as the first staged cannabinoid composition 804 but in different ratios. For example, the first staged cannabinoid composition 804 may contain THC and CBD in a ratio of 10:1 while the second staged cannabinoid composition 810 may contain THC and CBD in a ratio of 1:1. Alternatively, different cannabinoids or additives may be included in the second staged cannabinoid composition 810 than in the first staged cannabinoid composition 804.

Further, embodiments may include the capsule filling module 118, shown as FIG. 9, which describes a method of filling a cannabinoid and/or psychoactive capsule. The process begins by receiving at step 902, a top and bottom half of an interior capsule. The interior capsule being smaller in size than the exterior capsule such that the interior capsule, or many interior capsules such as microencapsulated beadlets, can fit within the exterior capsule in addition to a first staged cannabinoid composition. In an embodiment, the interior capsule shells are made of gelatin. Filling at step 904, the bottom half of the interior capsule with a measured dose of the second staged cannabinoid composition. The second staged cannabinoid composition containing at least one cannabinoid and an additive. In an embodiment, the interior capsule being filled with a second staged cannabinoid composition comprised of THC and CBD in a ratio of 1:1 and acetaminophen as an additive. Pressing at step 906, the halves of the filled interior capsule together such that the top and bottom halves of the interior capsule are firmly held in place by friction. In an embodiment, an indentation may be made along the overlapping portion of the top and bottom halves of the interior capsule to create a crimp, improving the reliability of the seal of the interior capsule. In an alternate embodiment, an adhesive may be applied to the exterior of the bottom half of the interior capsule such that when pressed together, the top half of the interior capsule slides over the bottom half of the interior capsule contacting the adhesive. Receiving at step 908, a top and bottom half of an exterior capsule. The exterior capsule being sufficiently larger in size than the sealed interior capsule such that the interior capsule can fit within the exterior capsule in addition to a first staged cannabinoid composition. In an embodiment, the exterior capsule halves are made of gelatin. Filling at step 910, the bottom half of the exterior capsule with a measured dose of the first staged cannabinoid composition. The first staged cannabinoid composition containing at least one cannabinoid and an additive. In an embodiment, the exterior capsule being filled with a first staged cannabinoid composition comprised of THC and CBD in a ratio of 10:1 and acetaminophen as an additive. The top half of the exterior capsule may additionally be filled. The first staged cannabinoid composition may be pressed into both the top and bottom halves of the exterior capsule to create a void located centrally within the exterior capsule sufficient to accommodate a sealed interior capsule. Inserting at step 912, a sealed interior capsule into the filled exterior capsule. The interior capsule being inserted into the void created in the first staged cannabinoid composition filling the bottom half of the exterior capsule. Pressing at step 914, the halves of the filled exterior capsule together such that the top and bottom halves of the interior capsule are firmly held in place by friction. The sealed exterior capsule fully encapsulating the first staged cannabinoid composition and a sealed interior capsule. In an embodiment, an indentation may be made along the overlapping portion of the top and bottom halves of the interior capsule to create a crimp, improving the reliability of the seal of the exterior capsule. In an alternate embodiment, an adhesive may be applied to the exterior of the bottom half of the exterior capsule such that when pressed together, the top half of the exterior capsule slides over the bottom half of the exterior capsule contacting the adhesive. In an alternate embodiment, the shell of the interior capsules can be formed concurrently with loading the interior capsules with active and inactive ingredients via sol-gel processes that precipitate microspheres upon changing the viscosity of the solution(s). In an alternate embodiment, the shell of the interior capsules can be formed concurrently with loading the interior capsules with active and inactive ingredients by utilizing a double nozzle system that produces concentric spheres of active ingredients and encapsulation formulations where the latter engulfs the former to produce a stable microsphere or beadlet.

FIG. 10 is a block diagram illustrating an overview of a system 1000 in accordance with embodiments of the disclosed technology. The system 1000 can be used to, for example, perform all or some of the steps discussed in connection with FIGS. 7 and 12 and can be a component (e.g., a controller) of a manufacturing system for manufacturing capsules discussed in connection with FIG. 9. The system 1000 can include one or more sensors 1018 and input devices 1020 that provide input to the processor(s) 1010 (e.g., CPU(s), GPU(s), HPU(s), etc.), notifying the processor(s) of, for example, event(s), operation, and/or actions. The input can be mediated by a hardware controller that interprets the signals received from the input device and communicates the information to the processors 1010 using a communication protocol. The events can include, without limitation, user input events, new available data events, formulation modification events, manufacturing events, or the like.

The processors 1010 can be a single processing unit or multiple processing units in a device or distributed across multiple devices. The processors 1010 can be coupled to other hardware devices, for example, with the use of a bus, such as a PCI bus or SCSI bus. The processors 1010 can communicate with a hardware controller for devices, such as for a display 1130. Display 1030 can be used to display text, graphics, chemical structures, formulation data, manufacturing data, etc. In some implementations, display 1030 provides graphical and/or textual visual feedback (e.g., formulation analytics, formulation efficacy projections, available user data, dosage information, dosing schedules, etc.). In some implementations, display 1030 includes the input device as part of the display, such as when the input device is a touchscreen. Examples of display devices are: an LCD display screen, an LED display screen, a projected or augmented reality display. Other I/O devices 1040 can also be coupled to the processor, such as user devices, biometric device, monitoring equipment, network card, video card, audio card, USB, firewire or other external device. The system 1000 also includes a communication device 1040 capable of communicating wirelessly or wire-based with a network node. The communication device can communicate with another device or a server through a network using, for example, TCP/IP protocols to acquire information, such as information discussed in connection with FIGS. 1-9. The system 1000 can utilize the communication device to distribute operations across multiple network devices.

The processors 1010 can access memory 1050 in a device or distributed across multiple devices. A memory includes one or more of various hardware devices for volatile and non-volatile storage and can include both read-only and writable memory. For example, a memory can comprise random access memory (RAM), various caches, CPU registers, read-only memory (ROM), and writable non-volatile memory, such as flash memory, hard drives, floppy disks, CDs, DVDs, magnetic storage devices, tape drives, and so forth. A memory is not a propagating signal divorced from underlying hardware; a memory is thus non-transitory. Memory 1050 can include program memory 1060 that stores programs and software, such as an operating system 1062, formulation or composition system 1064 ("composition system 1064"), and other application programs 1066. Memory 1050 can also include data memory 1070, e.g., authentication information, database access information, configuration data, settings, user options or preferences, etc., which can be provided to the program memory 1050 or any element of the system 1000.

The system 1000 be configured for machine learning model(s). The machine learning models can be of various types, such as Convolutional Neural Networks (CNNs), other types of neural networks (e.g., fully connected), decision trees, forests of classification trees, Support Vector Machines, etc. Machine learning models can be trained to produce particular types of results, operations, etc. For example, a training procedure can include obtaining suitable training items with input associated with a result, applying each training item to the model, and updating model parameters based on comparison of model result to training item result. The machine learning model(s) can be generated by, for example, the cloud system using data from databases. Example machine learning models are discussed in connection with FIG. 12 and can design compositions, identify correlations between compositions, etc.

Figure 11:
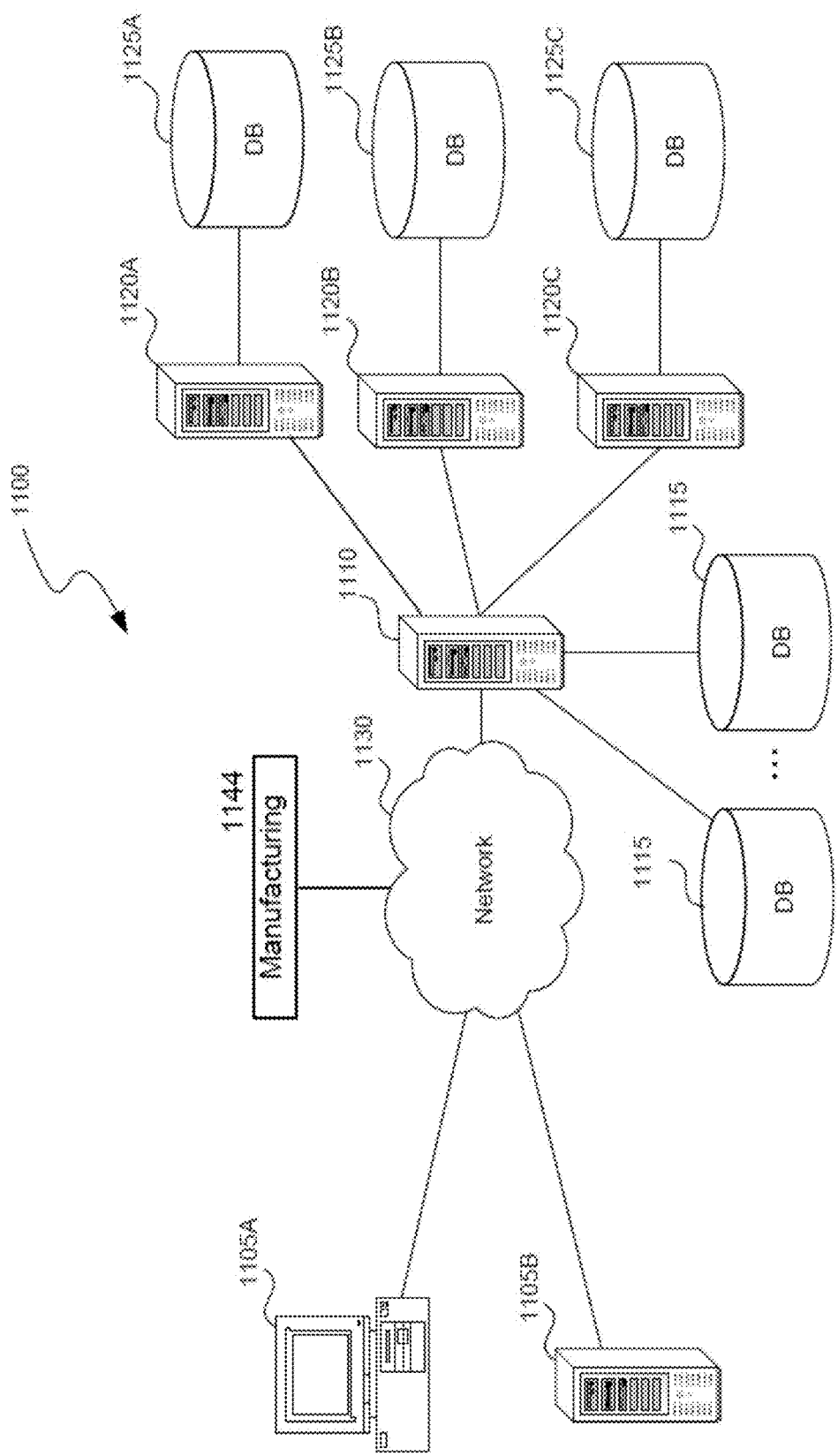
FIG. 11 is a block diagram illustrating an overview of an environment in which some implementations can operate.

FIG. 11 is a block diagram illustrating an overview of an environment or system 1100 ("system 1100") in which some implementations of the disclosed technology can operate. System 1100 can include one or more client computing devices 1105A-B. Client computing devices 1105A-B can operate in a networked environment using logical connections through network 1130 to one or more remote computers, such as a server computing device. The client computing devices 1105A-B can request, for example, personalized formulations, treatment protocols, compositions, composition analytics, patient records, etc.

In some implementations, server 1110 can receive client requests and coordinates fulfillment of those requests (e.g., personalized formulation orders, patient monitoring, etc.) through other servers, such as servers 1120A-C. Server computing devices 1110 and 1120A-C can comprise computing systems, such as device or system 1000 of FIG. 10. Though each server computing device 1110 and 1120A-C is displayed logically as a single server, server computing devices can each be a distributed computing environment encompassing multiple computing devices located at the same or at geographically disparate physical locations. In some implementations, each server 1120A-C corresponds to a group of servers.

Client computing devices 1105A-B and server computing device 1110 and 1120 can each act as a server or client to other server/client devices. Server 1110 can connect to one or more databases 1115. Servers 1120A-C can each connect to a corresponding database 1125A-C (collectively "databases 1125"). As discussed above, each server 1120 can correspond to a group of servers, and each of these servers can share a database or can have their own database. Databases 1115 and 1125 can store information, such as data discussed in connection with FIGS. 1-6 and other information disclosed herein. Though databases 1115 and 1125 are displayed logically as single units, databases 1115 and 1125 can each be a distributed computing environment encompassing multiple computing devices, can be located within their corresponding server, or can be located at the same or at geographically disparate physical locations. In some embodiments, the databases 1115 store patient data and can include, without limitation, sleep databases (e.g., database 112 of FIG. 1), biometric databases (e.g., biometric data from healthcare providers, wearable biometric devices), patient health databases, ERM databases, etc. The databases 1125 can include, without limitation, the composition databases 104, analgesic databases 106, bioavailability databases 108, and other databases disclosed herein. The server 1110 can acquire data from selected data bases to develop compositions.

Network 1130 can be a local area network (LAN), a wide area network (WAN) or other wired or wireless networks. Network 1130 may be the Internet or some other public or private network. Client computing devices 1105 can be connected to network 1130 through a network interface, such as by wired or wireless communication. While the connections between server 1110 and servers 1120 are shown as separate connections, these connections can be any kind of local, wide area, wired, or wireless network, including network 1130 or a separate public or private network.

The system 1000 can perform the steps discussed herein. For example, the server 1110 can function as the capsule module 114 (FIGS. 1 and 7) configured to formulate, for example, capsules for the subject by selecting specific excipients and other nonactive ingredients that are compatible with the active ingredients. The system 100 can retrieve data from one or more of the databases 1125A-C. The system 1000 can generate, store, train (including retraining), and/or modify one or more machine learning models, as discussed in connection with FIG. 12. In some embodiments, the system 1000 can generate formations for recreational and medicinal cannabis formulations that comply with regulations, laws, and medical reimbursements. One or more of the databases 1125A-C can include, for example, regulations, laws, and medical reimbursements that are accessed based on the user's location, shipping information, etc. The system 100 can design cannabinoid compositions having improved, better controlled bioavailability. The number, type, and data structure of the databases 1115, 1125 can be selected based on the formulation design process.

The system 1100 can determine whether to manufacture multi-staged release compositions based on availability of suitable premade compositions. The server 1110 can be programmed to identify, order, and/or provide access to available compositions (e.g., preexisting or premade formulations in inventory, non-subject-specific formulations, etc.) to avoid or limit manufacturing times, subject-specific composition manufacturing costs, etc. In response to client requests, the system 1100 can send a notification from the server 1110 indicating the availability of the suitable composition. In some embodiments, the system 1100 (e.g., server 1110 or other servers) can query one or more of the databases 1125A-1125C storing inventory data, data of premade multi-staged release compositions (e.g., compositions in stock at local pharmacies, distribution centers, dispensaries, etc.), historical subject/user data, or the like. In some embodiments, the stored data can include, for example, inventory information (e.g., quantity of premade formulations), expiration information, composition of formulations, release profiles of compositions, manufacturing dates, manufacture information, ingredient lists, dosage forms, historical patient outcomes, and other information. The databases 1125A-1125C can store data disclosed herein, such as dosing models (e.g., subject-specific dosing models), subject/user data (e.g., electronic health records, physician notes, subject/user feedback, subject/user biometric data, etc.), sets of composition data, combinations thereof, or the like. Sets of composition data can include, without limitation, ingredient lists, percentages of ingredients, dosage forms, manufacturing instructions, or the like.

The system 1100 can determine whether compositions (e.g., multi-staged release compositions in inventory) are acceptable for a subject based on, for example, one or more multi-staged release profiles for that subject, maximum dosages for the subject, minimum dosages for the subject, input (e.g., physician input, healthcare provider input, etc.), or the like. In some implementations, the system 1100 can rank inventory based on a matching score. The system 1100 can compare a target multi-staged release profile of the subject to release profile of premade compositions to determine whether they match based on, for example, one or more matching criterion. The matching criterion can be inputted by, for example, a user, a physician, a healthcare provider, or the like. If the release profile of the premade composition is within an acceptable range of the planned release profile, the system 1100 can identify a match. The user can then be notified that a matching composition is in inventory, and the notification can include access information. The access information can include, without limitation, inventory location information, purchasing information, manufacturing information, links to vendor websites, dispensary information, prescription information, combinations thereof, or the like. In some embodiments, the system 1100 transmits a prescription via the network 1130 to a pharmacy computer 1105B. The user can then purchase the product at the pharmacy.

In response to the system 1100 determining that no suitable premade composition is available, the system 1100 can generate and send, via the network 1130, instructions for manufacturing to a manufacturer 1144. The instructions can include, without limitation, dosage form, number of compositions, percentages of compositions, manufacturing or processing steps, or other information suitable for use in manufacturing the multi-staged release composition. In some embodiments, the system 1100 uses one or more machine learning models to determine the manufacturing instructions, and the machine learning model can be trained using manufacturing data sets including manufacturing quality data. The system 1100 can identify acceptable compositions in inventory based on one or more criterion for the cannabinoid therapy. The criterion can include, without limitation, one or more release profiles, dosage ranges, manufacturer information, grower data, cannabinoid processing criterion, etc.

In some embodiments, the system 1100 can determine whether to manufacture a subject-specific multi-staged release composition based on an availability or inventory schedule of compositions. If acceptable premade compositions will be available within a desired period of time, the system 1100 can notify the subject of their availability. In some embodiments, the system 1100 can query inventory databases to identify acceptable compositions in inventory. The system 1100 can then send notifications identifying the available compositions for review by the subject. If a user (or physician, healthcare worker, etc.) approves the identified available composition, the system 1100 can order or provide purchasing instructions. If the user rejects the identified composition, the system 1100 can identify alternative compositions in inventory for user review and approval. If the user wants a subject-specific formulation, the user can select on-demand manufacturing of the user-specific formulation.

The system 1100 can use techniques disclosed herein to determine one or more cannabinoid therapies based on, for example, physician input, user input, user biometrics, prior patient outcomes, or the like. Prior patient outcomes can be selected based on matching cannabinoid therapies, subject/user conditions, etc. Cannabinoid therapies can include, without limitation, therapies for neurological diseases (e.g., Parkinson's disease, Huntington's disease, Alzheimer's, multiple sclerosis, etc.), anorexia, irritable bowel syndrome, pain management, psychological disorders, or the like. The system 1100 can generate a patient-specific dosing model complementing or matching criteria of the cannabinoid therapy for treating a therapeutic condition based pm the prior patient outcomes.

Figure 12:
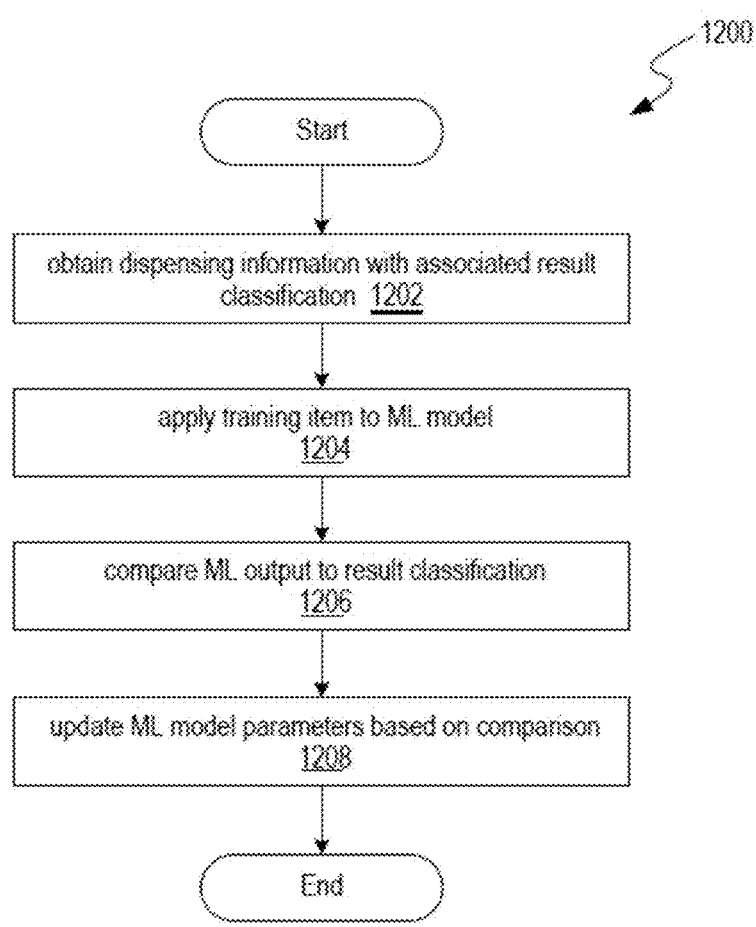
FIG. 12 illustrates a flowchart showing a method for training a machine learning model, according to an embodiment.

FIG. 12 illustrates a flowchart showing a method 1200, in accordance with some embodiments. Machine learning models, such as neural networks, can be trained to produce types of results. A neural network can be trained by obtaining, at block 1202, a quantity of "training items," where each training item includes input similar to input the model will receive when in use and a corresponding scored result. At block 1204, the input from each training item can be supplied to the model to produce a result. At block 1206, the result can be compared to the scored result. At block 1208, model parameters can then be updated, based on how similar the model result is to the scored result and/or whether the score is positive or negative. The method 1200 can be used to generate one or more trained machine learning models for outputting any of the following: composition, formulation, manufacturing process, dosing schemes, therapeutically effective amounts for a specific user, prediction of a future value of the health parameter within a period of time, prediction of therapeutic effect, predictions for avoiding adverse events, etc. The steps of the method 1200 can be selected based on the inputs and desired output and are discussed below.

At block 1202, model input can include, without limitation, stored data (e.g., data from databases 104, 106, 108, 110, 112, 114 of FIGS. 1-6), composition information, cannabinoid preferences, user-specific input (e.g., sensitivity level(s) to active agent sensitivity, analgesic sensitivity, bioenhancer sensitivity, etc.), caregiver input, and so forth. The training data input can be classified and/or paired with results to create training items. The classification can be selected based on the model characteristics and output. The results for training items can be, for example, user feedback to model outputs, healthcare provided suggestion feedback (e.g., whether the healthcare accepted model provided recommendations completely, or made certain changes, or disregarded), user rating or scoring of doses, biometric data analyzed to determine results, the existence of certain positive or negative user experiences, or the like. The product input can include, without limitation, characteristics disclosed herein, such as number of staged releases, length of each staged release, release profiles, target efficiency, user input, and so forth. The user input can include, without limitation, objective data, such as personal data collected by biometric or wearable devices. The user feedback may result in refined personal dosing schemes, recommended compositions/formulas, etc. The data discussed in connection with FIGS. 1-11 can be used as model input, model selection, etc. The input, subject scoring, and other information can be collected via, for example, a user device (e.g., user devices 1105A, 1105A of FIG. 11), input/output devices (e.g., input/output devices 1040 of FIG. 10), etc. In some embodiments, user feedback is aggregated. Aggregated user feedback may be used to develop and refine a heuristic algorithm to provide schemes, recommendations, etc., to new users, users using new substances, or the like.

At block 1204, input from each training item can be supplied to the model to produce a result or output. The output can be converted to arrays of integers that, when provided to the machine learning model, produce values that specify dosing schemes, device settings, etc. Any number of models can be generated to recommend dosing schemes, products for purchase, recommended flavoring products, etc.

At block 1206, results can be compared to the scored result or result classification. For example, result dosing schemes can be compared to actual dosing schemes used by users that produced the training item. The model can correlate composition information to predicted user experience or outcome. The composition information can release profiles, effect profiles, active agent characteristics, active agent interaction (e.g., interaction between multiple active agents), formulation characteristics, etc.

At block 1208, model parameters can be updated, based on how similar the model result is to the scored result and/or whether the score is positive or negative. The model parameters can then be adjusted so the model output is more like the prior formulation or dosing scheme and user experience if that prior user experience was a success or less like the prior dosing scheme, if the prior user experience was unsuccessful (e.g., undesired effect). The amount of adjustment to the model parameters can be a function of how different the model prediction was from the actual dosing scheme used and/or the level of success or failure of the product usage. Machine learning models can be trained to produce various results, determine dosing schemes (e.g., constant or variable dosing schemes), or the like. Models can be grouped or classified based on user characteristics, such as user sensitivity to active agents.

The method 1200 can generate dispensing schemes based on formulation form (e.g., pill, tablet, capsule, etc.), a user's profile, previous sensor data for that user, and/or information and/or sensor data from a plurality of other users. In some embodiments, a health state is quantified as a score or metric representing the user's overall health status and/or risk, which can be generated based on any suitable combination of sensor data and/or other data. In some embodiments, user-specific setting or recommendations may be based upon, for example, the health state, specific user's experience feedback, etc. The user experience feedback may query the user for a variety of parameters. A model can be trained using sets of user feedback, flavor profiles, dosage information, composition information, volumes, temperatures (e.g., active ingredient temperatures, flavor compound temperatures, etc.), type of administration (e.g., oral, transmucosal, etc.), and corresponding scores for usage.

The method 1200 can be used to train machine learning models for different dosage form. For example, one machine learning model can be used to formulate pills. Another machine learning model can be used to generate a formulation for capsules. Yet another machine learning model can be used to generate a formulation for topical or transdermal patches. In some embodiments, the systems disclosed herein can receive dosage form input. The system can then select a machine learning model based on the received dosage form. The system can retrieve data from a database associated with a form, user data, etc. In some embodiments, the retrieved data can be selected based on historical patient data for patients with similar or matching health profiles.

In some embodiments, multiple machine learning training procedures can be performed. Example procedures can include obtaining suitable training data set associated with a result, applying each training data set to the model, and updating model parameters based on comparison of model result to training set result. Each model can be designed for a different result. A neural network can be trained by obtaining a quantity of "training items or data set," where each training item or data set includes input similar to input the model will receive when in use and a corresponding scored result. The input from each training item/data set can be supplied to the model to produce a result. The result can be compared to the scored result. Model parameters can then be updated based on how similar the model result is to the scored result and/or whether the score is positive or negative. A training procedure can include clustering, predictive analysis, etc. as discussed above. The training procedure can be selected based on the amount, quality, and/or characteristics of the data.

In accordance with some embodiments, a computer implemented method for a multi-staged release composition for cannabinoid therapy includes storing data associated with a subject and generating a subject-specific dosing model for the subject based on the stored data. The method also includes determining a multi-stage release profile according to the generated subject-specific dosing model. The method includes selecting a dosage form for the multi-staged release composition based on the determined multi-stage release profile. The method includes determining two or more compositions staged for release at different times and/or with different release profiles based on the dosage form and the multi-stage release profile. The two or more compositions comprise one or more active agents comprising cannabinoids, one or more bioavailability enhancer, or both. The method also includes storing a set of data for the multi-staged release composition in a database. The set of data includes the two or more compositions and the dosage form.

In some embodiments, the method includes generating the subject-specific dosing model by using a machine learning technique. Generating the subject-specific dosing model includes obtaining classified training items. The classified training items include training data paired with a set of outcomes. The set of outcomes includes multiple levels of therapeutic effects achieved by treatment of training subjects with multi-staged release compositions. The therapeutic effects can be associated with a therapeutic condition selected from at least one of alleviating pain, providing energizing effects, increasing appetite, assisting with sleep, stimulating introspection, or aiding meditative practice. Generating the subject-specific dosing model includes applying the classified training items to a machine learning algorithm to generate the subject-specific dosing model.

In some embodiments, the method further includes comparing the generated subject-specific dosing model to the training data paired with the set of classifications and updating the subject-specific dosing model based on the comparison.

In some embodiments, the training data includes subject data of training subjects. The subject data of training subjects includes one or more of a therapeutic condition associated with a respective training subject and one or more of sleep data associated with the respective training subject, biometric data associated with the respective training subject, input from the respective training subject, input from a physician associated with the respective training subject, and retrieved data from an electronic medical record for the respective training subject.

In some embodiments, the training data includes one or more of a number of stages, a length of stages, dosage amounts, and/or data associated with the treatment of the training subjects with the multi-staged release compositions.

In some embodiments, the method further includes determining whether an acceptable premade multi-staged release composition is available for the subject based on the multi-stage release profile. The premade multi-staged release composition includes the determined two or more compositions. In response to determining the premade multi-staged release composition is available, the method includes providing access information for the premade multi-staged release composition to the subject. In response to determining that the premade multi-staged release composition is not available, the method includes sending instructions for manufacturing the multi-staged release composition for the subject.

In some embodiments, the method further comprises comparing the multi-stage release profile to a release profile of the premade multi-staged release composition to determine whether the premade multi-staged release composition is acceptable for the subject.

In some embodiments, the method further comprises matching the premade multi-staged release composition to the subject based on at least one cannabinoid therapy criterion.

In some embodiments, the method further includes querying at least one inventory database of multi-staged release compositions to identify an acceptable multi-staged release composition in inventory. The method also includes sending a notification for the subject of the identified acceptable multi-staged release composition for the subject.

In some embodiments, the method further comprises determining a cannabinoid therapy model based on prior patient cannabinoid therapy outcomes for prior patients that match the subject. The generation of the subject-specific dosing model is based on the cannabinoid therapy and a therapeutic amount at least one of the two or more compositions.

In some embodiments, the method further includes determining whether to manufacture a subject-specific multi-staged release composition based on an availability schedule of acceptable non-subject-specific multi-staged release composition for the subject.

In some embodiments, determining the multi-stage release profile for the multi-staged release composition includes matching the multi-stage release profile to the subject-specific dosing model.

In some embodiments, the dosage form includes a pill, a tablet, a capsule, a transdermal patch, a transmucosal patch, a lozenge, intranasal formulation, or a suppository.

In some embodiments, the multi-stage release profile includes: a number of stages, lengths of respective stages, amount of dosage for the respective stages, and tapering for the respective stages.

In some embodiments, receiving the subject data of the subject includes receiving biometric data obtained by a wearable electronic device worn by a subject.

In some embodiments, receiving the subject data of the subject includes receiving biometric data obtained from the subject using a wearable electronic device.

In accordance with some embodiments, a system for manufacturing a multi-staged release composition includes a composition manufacturing system configured to manufacture unit dosage forms and a dosage designing server system. The dosage designing server system is in communication with a user device and the composition manufacturing system. The dosage designing server system is programmed to receive, from the user device, a user request for an indication of two or more compositions staged for release for treatment of a therapeutic condition of a subject. In response to the user request, receive subject data of the subject. The subject data includes data retrieved from one or more databases of the server system, and input received from the respective user device. The server system is programmed to analyze the subject data to generate a dosing model and determine a multi-stage release profile for the multi-staged release composition according to the dosing model. The server system is programmed to select a dosage form for the multi-staged release composition based on the multi-stage release profile. The server system is also programmed to determine the two or more compositions staged for release at different times or with different release profiles based on the dosage form and the multi-stage release profile. One or more staged compositions comprise one or more active agents comprising cannabinoids, one or more bioavailability enhancer, or both. The server system is programed to send instructions to the composition manufacturing system to manufacture unit doses of the multi-staged release composition in accordance with the indication of the two or more compositions staged for release.

In some embodiments, the user device is an electronic device associated with the subject.

In some embodiments, the user device is an electronic device associated with a physician treating the subject.

In some embodiments, causing, by the dosage designing server system, the composition manufacturing system to manufacture the multi-staged release composition in accordance with the with the indication of the two or more compositions staged for release.

In some embodiments, dosage designing server system is configured to cause the composition manufacturing system to manufacture the multi-staged release composition in accordance with the with the indication of the two or more compositions staged for release.

In an illustrative embodiment, any of the operations, processes, etc., described herein can be implemented as computer-readable instructions stored on a computer-readable medium. The computer-readable instructions can be executed by a processor of a mobile unit, a network element, and/or any other computing device.

Some implementations can be operational with numerous other computing system environments or configurations. Examples of computing systems, environments, and/or configurations that may be suitable for use with the technology include, but are not limited to, personal computers, server computers, handheld or laptop devices, cellular telephones, wearable electronics, gaming consoles, tablet devices, multiprocessor systems, microprocessor-based systems, set-top boxes, programmable consumer electronics, network PCs, minicomputers, mainframe computers, distributed computing environments that include any of the above systems or devices, or the like.

The functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

From the foregoing, it will be appreciated that specific embodiments of the invention have been described herein for purposes of illustration, but that various modifications may be made without deviating from the scope of the invention. Accordingly, the invention is not limited except as by the appended claims.

What is claimed is:

1. A computer-implemented method for a multi-staged release composition for cannabinoid therapy, the method comprising:
   storing data associated with a subject;
   generating, using a machine learning engine, a subject-specific dosing model for the subject based on the stored data by
      obtaining classified training items, wherein the classified training items include training data paired with a set of outcomes, wherein the set of outcomes includes multiple levels of therapeutic effects achieved by treatment of training subjects with multi-staged release compositions, the therapeutic effects associated with a therapeutic condition selected from at least one of alleviating pain, providing energizing effects, increasing appetite, assisting with sleep, stimulating introspection, or aiding meditative practice; and
      applying the classified training items to a machine learning algorithm to generate the subject-specific dosing model, wherein the subject-specific dosing model includes a correlation between information associated with the composition for the cannabinoid therapy and a predicted user experience or outcome for the subject based on prior treatment outcomes;
   determining a multi-stage release profile according to the generated subject-specific dosing model;
   selecting a dosage form for the multi-staged release composition based on the determined multi-stage release profile;
   determining two or more compositions staged for release at different times and/or with different release profiles based on the dosage form and the multi-stage release profile, wherein two or more compositions comprise one or more active agents comprising cannabinoids, one or more bioavailability enhancer, or both; and
   storing a set of data for the multi-staged release composition in a database, wherein the set of data includes the two or more compositions and the dosage form.

2. The method of claim 1, further comprising:
   comparing the generated subject-specific dosing model to the training data paired with the set of outcomes; and
   updating the subject-specific dosing model based on the comparison.

3. The method of claim 1, wherein:
   the training data includes subject data of training subjects, the subject data of training subjects including one or more of a therapeutic condition associated with a respective training subject and one or more of sleep data associated with the respective training subject, biometric data associated with the respective training subject, input from the respective training subject, input from a physician associated with the respective training subject, and retrieved data from an electronic medical record for the respective training subject.

4. The method of claim 1, wherein:
   the training data includes one or more of a number of stages, a length of stages, dosage amounts, and data associated with the treatment of the training subjects with the multi-staged release compositions.

5. The method of claim 1, further comprising:
   determining whether an acceptable premade multi-staged release composition is available for the subject based on the multi-stage release profile, wherein the premade multi-staged release composition includes the determined two or more compositions;
   in response to determining the premade multi-staged release composition is available, providing access information for the premade multi-staged release composition to the subject; and
   in response to determining the premade multi-staged release composition is not available, sending instructions for manufacturing the multi-staged release composition for the subject.

6. The method of claim 5, further comprising comparing the multi-stage release profile to a release profile of the premade multi-staged release composition to determine whether the premade multi-staged release composition is acceptable for the subject.

7. The method of claim 6, further comprising matching the premade multi-staged release composition to the subject based on at least one cannabinoid therapy criterion.

8. The method of claim 1, further comprising:
   querying at least one inventory database of multi-staged release compositions to identify an acceptable multi-staged release composition in inventory; and
   sending a notification for the subject of the identified acceptable multi-staged release composition for the subject.

9. The method of claim 1, further comprising determining a cannabinoid therapy model based on prior patient cannabinoid therapy outcomes for prior patients that match the subject, wherein the generation of the subject-specific dosing model is based on the cannabinoid therapy and a therapeutic amount at least one of the two or more compositions.

10. The method of claim 1, further comprising determining whether to manufacture a subject-specific multi-staged release composition based on an availability schedule of acceptable non-subject-specific multi-staged release composition for the subject.

11. The method of claim 1, wherein determining the multi-stage release profile for the multi-staged release composition includes matching the multi-stage release profile to the subject-specific dosing model.

12. The method of claim 1, wherein the dosage form includes a pill, a tablet, a capsule, a transdermal patch, a transmucosal patch, a lozenge, intranasal formulation, or a suppository.

13. The method of claim 1, wherein the multi-stage release profile includes:
  a number of stages, lengths of respective stages, amount of dosage for the respective stages, and tapering for the respective stages.

14. The method of claim 1, wherein:
  receiving the subject data of the subject includes receiving biometric data obtained by a wearable electronic device worn by a subject.

15. The method of claim 1, wherein:
  receiving the subject data of the subject includes receiving input from a subject or a physician associated with the subject.

16. The method of claim 1, wherein:
  receiving the subject data of the subject includes receiving biometric data obtained from the subject using a wearable electronic device.

17. A system comprising one or more processors and a memory including instructions for a multi-staged release composition for cannabinoid therapy, the instructions which, when executed by the one or more processors, cause the system to:
  store data associated with a subject;
  generate, using a machine learning engine, a subject-specific dosing model for the subject based on the stored data by
    obtaining classified training items, wherein the classified training items include training data paired with a set of outcomes, wherein the set of outcomes includes multiple levels of therapeutic effects achieved by treatment of training subjects with multi-staged release compositions, the therapeutic effects associated with a therapeutic condition selected from at least one of alleviating pain, providing energizing effects, increasing appetite, assisting with sleep, stimulating introspection, or aiding meditative practice; and
    applying the classified training items to a machine learning algorithm to generate the subject-specific dosing model, wherein the subject-specific dosing model includes a correlation between information associated with the composition for the cannabinoid therapy and a predicted user experience or outcome for the subject based on prior treatment outcomes;
  determine a multi-stage release profile according to the generated subject-specific dosing model;
  select a dosage form for the multi-staged release composition based on the determined multi-stage release profile;
  determine two or more compositions staged for release at different times and/or with different release profiles based on the dosage form and the multi-stage release profile, wherein two or more compositions comprise one or more active agents comprising cannabinoids, one or more bioavailability enhancer, or both; and
  store a set of data for the multi-staged release composition in a database, wherein the set of data includes the two or more compositions and the dosage form.

18. The system of claim 17, wherein the system is further caused to:
  determine whether an acceptable premade multi-staged release composition is available for the subject based on the multi-stage release profile, wherein the premade multi-staged release composition includes the determined two or more compositions;
  in response to determining the premade multi-staged release composition is available, provide access information for the premade multi-staged release composition to the subject; and
  in response to determining the premade multi-staged release composition is not available, send instructions for manufacturing the multi-staged release composition for the subject.

19. A computer-implemented method comprising:
  generating a subject-specific dosing model by:
    training a machine learning model by applying classified training items to the machine learning model, wherein the classified training items are based on one or more therapeutic effects achieved by multi-staged release compositions treatments on training subjects, wherein the one or more therapeutic effects are associated with at least one of alleviating pain, providing energizing effects, increasing appetite, assisting with sleep, stimulating introspection, or aiding meditative practice, and
    applying stored data of a subject to the trained machine learning model to generate the subject-specific dosing model, wherein the subject-specific dosing model includes at least one predicted experience or outcome for the subject;
  selecting a dosage form for the multi-staged release composition based on the subject-specific dosing model;
  determining two or more compositions staged for release at different times and/or with different release profiles based on the dosage form, wherein at least one of the two or more compositions comprises one or more active agents comprising cannabinoids, one or more bioavailability enhancer, or both; and
  storing a set of data for the multi-staged release composition in a database, wherein the set of data includes the two or more compositions and the dosage form.

20. The computer-implemented method of claim 19, further comprising generating a subject-specific multi-stage release profile based on the subject-specific dosing model, wherein the subject-specific multi-stage release profile is used to select the dosage form.

21. The computer-implemented method of claim 19, wherein the at least one predicted experience or outcome includes
  one or more predicted experiences for the subject, and
  one or more predicted outcomes for the subject.

22. A system comprising one or more processors and a memory including instructions for a multi-staged release composition for cannabinoid therapy, the instructions which, when executed by the one or more processors, cause the system to:
   generate a subject-specific dosing model by
      train a machine learning model by applying classified training items to the machine learning model, wherein the classified training items are based on therapeutic effects achieved by multi-staged release compositions treatments on training subjects, wherein the therapeutic effects are associated with at least one of alleviating pain, providing energizing effects, increasing appetite, assisting with sleep, stimulating introspection, or aiding meditative practice, and
      applying stored data of a subject to the trained machine learning model to generate the subject-specific dosing model, wherein the subject-specific dosing model includes at least one predicted experience or outcome for the subject;
   select a dosage form for the multi-staged release composition based on the determined subject-specific dosing model;
   determine two or more compositions staged for release at different times and/or with different release profiles based on the dosage form, wherein at least one of the two or more compositions comprises one or more active agents comprising cannabinoids, one or more bioavailability enhancer, or both; and
   store a set of data for the multi-staged release composition in a database, wherein the set of data includes the two or more compositions and the dosage form.

23. The system of claim 22, wherein the system is further configured to generate a subject-specific multi-stage release profile based on the subject-specific dosing model, wherein the subject-specific multi-stage release profile is used to select the dosage form.

\* \* \* \* \*